United States Patent [19]

King et al.

[11] 4,166,184

[45] Aug. 28, 1979

[54] 2H-IMIDAZOLE-2-THIONE DERIVATIVES

[75] Inventors: Ronald J. King, Wareside; George R. White, Harpenden, both of England

[73] Assignee: Smith Kline & French Laboratories Limited, Welwyn Garden City, England

[21] Appl. No.: 858,488

[22] Filed: Dec. 8, 1977

[30] Foreign Application Priority Data

Dec. 22, 1976 [GB] United Kingdom ............... 53538/76

[51] Int. Cl.² .......................................... C07D 233/84
[52] U.S. Cl. ............................. 548/321; 260/307 A; 260/558 R; 260/558 P; 260/584 A
[58] Field of Search ......................................... 548/321

[56] References Cited

U.S. PATENT DOCUMENTS 2,585,388  11/1948  Jones .................................... 548/321
3,361,752  1/1968  Dunbar ................................. 548/321

OTHER PUBLICATIONS

Theilheimer Synthetic Methods of Organic Chemistry, vol. 8, 1954, p. 161.
Pyman, J. Chem. Soc., 98–100 (1930).
Alles, C.A. 14693, 1957, vol. 51.
Mosebach, C.A., 11639e, vol. 55.
Bullerwell et al., C.A., vol. 46, 9096F.
Lawson et al., Biochem J., 59: 1955, p. 345 and 49: 1951, p. 125.
Stanacev et al., Chem. Abst. 51:11995d, 61:13249a, 62:14577b, 64:3428e and 66:55478e.
Steglich et al., Angrew. Chem. Internat. Edit. 8:982 (1969).

*Primary Examiner*—Natalie Trousof
*Assistant Examiner*—Jane T. Fan
*Attorney, Agent, or Firm*—Joan S. Keps; Richard D. Foggio; William H. Edgerton

[57] ABSTRACT

Imidazole derivatives which are useful intermediates for the production of compounds having pharmacological activity at histamine $H_2$ receptors. A specific compound of the present invention is 4-(4-aminobutyl)-1,3-dihydro-5-methyl-2H-imidazole-2-thione, hereinafter referred to as 4-(4-Aminobutyl)-5-methylimidazole-2-thione.

3 Claims, No Drawings

2H-IMIDAZOLE-2-THIONE DERIVATIVES

This invention relates to imidazole derivatives and in particular to certain 4,5-disubstituted imidazole-2-thiones of the following Formula I:

$$\text{R}-\text{C}(=\text{C}(\text{CH}_2)_n\text{NHQ})-\text{HN}-\text{C}(=\text{S})-\text{NH}$$

FORMULA I wherein R is methyl or ethyl; n is 2,3,4 or 5; and Q is hydrogen or an aroyl group such as benzoyl. The compounds of the invention can exist as acid addition salts, but, for convenience, reference will be made throughout this specification to the parent compounds.

The compounds of Formula I are useful intermediates for the production of compounds having pharmacological activity at histamine $H_2$ receptors. This activity may be either as agonists or as antagonists. Desulphurisation of the compounds of Formula I with, for example, Raney nickel in ethanol yields the compounds of Formula II:

$$\text{R}-\text{C}(=\text{C}(\text{CH}_2)_n\text{NHQ})-\text{HN}-\text{CH}=\text{N}$$

FORMULA II wherein R, n and Q have the above significance. The compounds of Formula II wherein n is 2 and Q is hydrogen, i.e., 4-methylhistamine and 4-ethylhistamine are $H_2$ agonists. The compounds of Formula II may also be converted to compounds having $H_2$-antagonist activity for example those described in U.S. Pat. Nos. 3,808,336 and 3,897,444.

Particularly useful compounds are those wherein R is methyl. Compounds wherein n is 4 are also preferred.

The compounds of Formula I may be produced from the corresponding diamino acids of Formula III:

$$\text{H}_2\text{N}(\text{CH}_2)_n\text{CH}(\text{COOH})(\text{NH}_2)$$

FORMULA III wherein n is 2,3,4 or 5 by the following reaction scheme wherein X is halogen, Ar is an aryl group such as phenyl and R, n and Q have the above significance.

$$\text{H}_2\text{N}(\text{CH}_2)_n\text{CH}(\text{COOH})(\text{NH}_2) \xrightarrow{\text{ArCOX or (ArCO)}_2\text{O}} \text{ArCONH}(\text{CH}_2)_n\text{CH}(\text{COOH})(\text{NHCOAr})$$

III → IV $$\xrightarrow{\text{Ac}_2\text{O or D.C.C.}} \text{V} \xrightarrow{\text{R COX or (RCO)}_2\text{O}} \text{VI}$$

V: Ar-oxazolone with (CH$_2$)$_n$NHCOAr
VI: Ar-oxazolone with COR and (CH$_2$)$_n$NHCOAr $$\xrightarrow[\text{(2. decarboxylate)}]{\text{1. mild hydrolysis}} \text{ArCONH}(\text{CH}_2)_n\text{CH}(\text{COR})(\text{NHCOAr}) \xrightarrow{\text{c HCl}} \text{QNH}(\text{CH}_2)_n\text{CH}(\text{COR})(\text{NH}_2)$$

VII → VIII $$\xrightarrow{\text{thiocyanate}} \text{R}-\text{C}(=\text{C}(\text{CH}_2)_n\text{NHQ})-\text{HN}-\text{C}(=\text{S})-\text{NH}$$

The diamino acid of Formula III is first reacted with aroyl halide or anhydride to yield the diaroylamino compound IV which is then reacted with a cyclising reagent such as acetic anhydride or preferably dicyclohexylcarbodiimide (D.C.C.) to give the oxazolone V. Reaction of this oxazolone with acetyl or propionyl halide or anhydride gives the compound VI and when this is subjected to mild hydrolysis e.g., with acetic acid, and subsequent spontaneous decarboxylation of the product, the compound of Formula VII under severe conditions e.g., with concentrated hydrochloric acid, removes one or both of the aroyl protecting groups and reaction of the resultant compound VIII with thiocyanate e.g., potassium thiocyanate yields the compound of Formula I.

The invention may be further illustrated with reference to the following Examples 1–5. Examples 6–11 show the preparation of compounds having activity at $H_2$ receptors from compounds of Formula I.

EXAMPLE 1

4-(4-Aminobutyl)-5-methylimidazole-2-thione hydrochloride (i) N,N'-Dibenzoyl lysine (140.4 g, 0.36 mol) dissolved in dioxan (350 ml) was added over 45 min to dicyclohexylcarbodiimide (88.0 g, 0.43 mol) in dioxan (193 ml). After stirring for 2 hours the mixture was set aside overnight, filtered from dicyclohexylurea (88.1 g), concentrated to half volume and added to H$_2$O. The precipitate was collected and recrystallised from methylal to give 4-(4-benzamidobutyl)-2-phenyl-5-oxazolone (104 g, 86%) m.p. 118°–122°.

Found: C, 71.1; H, 6.2; N, 8.7. C$_{20}$H$_{20}$N$_2$O$_3$ requires: C, 71.4; H, 6.0; N, 8.3.

(ii) A mixture of the oxazolone (1.69 g, 0.005 mol), 4-dimethylaminopyridine (0.025 g), acetic anhydride (1 ml) and triethylamine (1 ml) was stirred until solution was obtained (one hour). Acetic acid (7.5 ml) was added and the solution was set aside overnight and evaporated to dryness. The residue was dissolved in chloroform and washed with dilute NaOH, dilute HCl and then dried over $MgSO_4$. Concentration gave the crude product which could be purified by dry-column chromatography on alumina with ethyl acetate as solvent to give, 3,7-dibenzamidoheptan-2-one (0.60 g, 34%). $\delta$(60 MHzDMSO-$d_6$) 8.5 (t,NH), ~8.3 (broad s,NH), ~7.8, 7.4(m,$C_6H_5$), 4.4 (m,CH), 3.2 (m,$NCH_2$), 2.1 (s,$CH_3$). 1.5 (m,$(CH_2)_3$).

(iii) Crude 3,7-dibenzamidoheptan-2-one (123 g, 0.35 mol) was hydrolysed by heating under reflux with concentrated HCl for 18 hours to give 3,7-diaminoheptan-2-one dihydrochloride (49 g, 65%), m.p. 160°–166° (MeCN). $\delta$(60 MHz$D_2O$) 4.3 (t,CH), 3.1 (t,$NHC_2$), 2.35 (s,$CH_3$), 1.7 (m($CH_2)_3$).

(iv) A solution of the aminoketone dihydrochloride (21.7 g, 0.10 mol) and potassium thiocyanate (19.40 g, 0.20 mol) in water was heated under reflux for 7 hours and then evaporated to dryness. The residue was extracted with hot AcOH, and the filtered extracts allowed to cool. The product obtained was recrystallised from acetic acid to give 4-(4-aminobutyl)-5-methylimidazole-2-thione hydrochloride (14.1 g, 64%), m.p. 279°–280°.

Found: C, 43.1; H, 7.2; N, 18.5; S, 13.9. $C_8H_{15}N_3S.HCl$ requires: C, 43.4; H, 7.3; N, 18.9; S, 13.9.

EXAMPLE 2

(i) 3,7-Dibenzamidoheptan-2-one (91.11 g, 0.258 mol) was hydrolysed in a sealed tube with concentrated HCl for 3 hours at 160° (oil bath). The solution was extracted with ether and evaporated to dryness to give 3-amino-7-benzamidoheptan-2-one hydrochloride (25.01 g, 34.2%).

(ii) A solution of 3-amino-7-benzamidoheptan-2-one hydrochloride (16.39 g, 0.0576 mol) and potassium thiocyanate (7.30 g, 0.0755 mol, excess) in water was heated under reflux for 20 hours. The aquesus phase was decanted off and the organic phase was washed with water, and recrystallised from acetonitrile to give 4-(4-benzamidobutyl)-5-methylimidazole-2-thione (4.18 g, 25%) m.p. 180°–184°.

Found: C, 62.01; H, 6.46; N, 14.39; S, 11.55%. $C_{15}H_{19}N_3OS$ requires: C, 43.3; H, 7.3; N, 18.9; S, 13.9.

EXAMPLE 3

4-(4-Aminobutyl)-5-ethylimidazole-2-thione hydrochloride

Reaction of 4-(4-benzamidobutyl)-2-phenyl-5-oxazolone according to the procedure of Example 1 (ii) but using propionic anhydride in place of acetic anhydride yields 4,8-dibenzamidooctan-3-one which on hydrolysis according to the procedure of Example 1 (iii) gives 4,8-diaminooctan-3-one. Reaction of this product with potassium thiocyanate according to the procedure of Example 1 (iv) gives the title compound.

EXAMPLE 4

(i) NN'-Dibenzoylornithine (29.09 g, 0.0855 mol) dissolved in dioxan (1160 ml) was treated by dropwise additon over 85 min. with dicyclohexylcarbodiimide (20.95 g, 0.102 mol) dissolved in dioxan (460 ml). The suspension was stirred for 22 hours, filtered from dicyclohexylurea (17.49 g), concentrated to half volume and added to $H_2O$. The precipitate was collected and recrystallised from toluene/petroleum ether (60°–80°) to give 4-(3-benzamidopropyl)-2-phenyl-5-oxazolone (18.55 g, 67%), m.p. 135°–138° C.

(ii) NN'-Dibenzoylornithine (0.05 g, 0.147 m.mol) and acetic anhydride (0.16 g, 1.57 m.mol) were heated at 155° C. for 7 minutes. The solution was evaporated to dryness and the residual white solid was recrystallised from benzene/petroleum ether (40°–60°) to give 4-(3-benzamidopropyl)-2-phenyl-5-oxazolone (0.02 g, 43%), m.p. 135°–138° C.

(iii) A mixture of 4-(3-benzamidopropyl)-2-phenyl-5-oxazolone (1.0 g, 3.1 m.mol), 4-dimethylaminopyridine (0.016 g), acetic anhydride (0.62 ml) and triethylamine (0.62 ml) was stirred for one hour. Acetic acid (4.7 ml) was added and the solution was set aside overnight and evaporated to dryness. The residue was dissolved in chloroform and washed with dilute NaOH, dilute HCl and then dried over $MgSO_4$. Concentration gave the crude product which could be purified by dry-column chromatography on alumina with ethyl acetate as solvent to give 3,6-dibenzamidohexan-2-one.

(iv) Substitution of 3,6-dibenzamidohexan-2-one for 3,7-dibenzamidoheptan-2-one in the procedure of Example 1 (iii) and (iv) gives 4-(3-aminopropyl)-5-methylimidazole-2-thione.

EXAMPLE 5

When, in the procedure of Example 1, the following starting materials are used in place of lysine:
2,4-dibenzoylamidobutyric acid
2,7-dibenzoylamidoheptanoic acid
the following compounds of the invention are produced:
4-(2-aminoethyl)-5-methylimidazole-2-thione,
4-(5-aminopentyl)-5-methylimidazole-2-thione.

EXAMPLE 6

Reaction of 4-(2-aminoethyl)-5-methylimidazole-2-thione with Raney nickel in ethanol yielded 4-methylhistamine.

EXAMPLE 7

(i) 4-(4-Aminobutyl)-5-methylimidazole-2-thione (14.1 g, 0.064 mole) in absolute ethanol (250 ml) was desulphurised with Raney nickel (approximately 25 g) for 30 minutes. Filtration followed by concentration under reduced pressure and treatment of the residue with HCl gave 4-(4-aminobutyl)-5-methylimidazole dihydrochloride (8.2 g), m.p. 206°–208° (from acetic acid).

Found: C, 42.4; H, 7.5; N, 18.2; Cl, 31.1. $C_8H_{15}N_3.2HCl$ requires: C, 42.5; H, 7.6; N, 18.6; Cl, 31.4.

(ii) A solution of the amine (obtained from the dihydrochloride (9.06 g, 0.049 mol) by basification with $K_2CO_3$, and methyl isothiocyanate (4.0 g, 0.055 mole) in EtOH (100 ml) containing a few drops of $H_2O$ was heated under reflux for 30 minutes. Filtration, followed by evaporation under reduced pressure and recrystallisation of the residue from MeCN gave N-methyl-N'[4-(5-methyl-4-imidazolyl)butyl]thiourea m.p. 110°–112° C. (from acetonitrile).

EXAMPLE 8

4-(4-Benzamidobutyl)-5-methylimidazole-2-thione (4.12 g, 0.01425 mol) in absolute ethanol (80 ml) was desulphrised with Raney nickel (approximately 18 g). Filtration followed by concentration under reduced pressure gave 4-(4-benzamidobutyl)-5-methylimidazole (3.23 g, 88%) m.p. 124°–128°.

4-(4-Benzamidobutyl)-5-methylimidazole is hydrolysed by heating with 6 N Hydrochloride Acid to give 4-(4-aminobutyl)-5-methylimidazole which may be converted into N-methyl-N'-[4-(5-methyl-4-imidazolyl)butyl]thiourea by the procedure of Example 7 (ii).

EXAMPLE 9

Reaction of 4-(4-aminobutyl)-5-methylimidazole (see Example 7 (ii), 2.71 g, 0.012 mol) with dimethylcyanodithioimidocarbonate (1.75 g 0.013 mol), gave S-methyl-N-cyano-N'-[4-(5-methyl-4-imidazolyl)butyl]isothiourea (2.27 g) which was treated directly with methylamine to yield N-cyano-N'-methyl-N''[4-(5-methyl-4-imidazolyl)butyl]guanidine (1.35 g), m.p. 152°–154° C. (from acetonitrile).

EXAMPLE 10

When 4-(3-aminopropyl)-5-methylimidazole-2-thione and 4-(5-aminopentyl)-5-methylimidazole-2-thione are desulphurised according to the procedure of Example 7 (i) the products are respectively 4-(3-aminopropyl)-5-methylimidazole and 4-(5-aminopentyl)-5-methylimidazole. By the procedure of Example 9 these compounds may be converted into N-cyano-N'-methyl-N''-[3-(5-methyl-4-imidazolyl)propyl]guanidine and N-cyano-N'-methyl-N''-[5-(5-methyl-4-imidazolyl)pentyl]guanidine respectively.

EXAMPLE 11

Reaction of 4-(4-aminobutyl)-5-methylimidazole (see Example 7 (ii), 0.765 g, 0.005 mol) with 1-methylsulphinyl-1-methylthio-2-nitroethylene(0.91 g, 0.005 mol), gave 1-methylthio-1-[4-(5-methylimidazol-4-yl)butylamino]-2-nitroethylene (0.69 g, 51%) which was treated directly with methylamine to yield 1-methylamino-b 1-[4-(5-methylimidazol-4-yl)butylamino]-2-nitroethylene (0.40 g, 61.9%). This compound was reacted with picric acid to give 1-methylamino-1-[4-(5-methylimidazol-4-yl)butylamino]-2-nitroethylene picrate hemihydrate (0.33 g, 26.3% last stage), m.p. 185°–187°.

What we claim is:

1. A compound of the following Formula I:

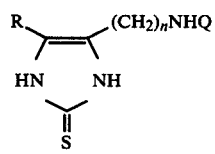

FORMULA I wherein R is methyl or ethyl; n is 2,3,4 or 5; Q is a benzoyl group; and the acid addition salts thereof.

2. A compound of claim 1 wherein R is methyl.
3. A compound of claim 1 wherein n is 4.

* * * * *